US007992100B2

(12) United States Patent
Lundström et al.

(10) Patent No.: US 7,992,100 B2
(45) Date of Patent: Aug. 2, 2011

(54) DYNAMIC SLABBING TO RENDER VIEWS OF MEDICAL IMAGE DATA

(75) Inventors: Claes Lundström, Linköping (SE); Per Anell, Bromma (SE); Fredrik Häll, Linköping (SE); Jonas Rehn, Danderyd (SE); Regina Rosander, Linköping (SE)

(73) Assignee: Sectra AB, Linkoping (SE)

( * ) Notice: Subject to any disclaimer, the term of this patent is extended or adjusted under 35 U.S.C. 154(b) by 891 days.

(21) Appl. No.: 11/956,422

(22) Filed: Dec. 14, 2007

(65) Prior Publication Data

US 2008/0155451 A1    Jun. 26, 2008

Related U.S. Application Data

(60) Provisional application No. 60/871,247, filed on Dec. 21, 2006.

(51) Int. Cl.
*G06F 3/048* (2006.01)
(52) U.S. Cl. ........ 715/810; 715/765; 715/781; 700/182; 382/131; 128/920; 128/922; 378/21; 378/37
(58) Field of Classification Search .................. 715/700, 715/764, 765, 810, 961, 964, 968, 781; 700/17, 700/65, 83, 84, 85, 98, 180, 182; 703/1; 705/3; 707/1, 10, 104.1, 705, 781, 805; 128/920, 128/922; 378/21, 37; 382/128, 131; 600/407
See application file for complete search history.

(56) References Cited

U.S. PATENT DOCUMENTS

| | | | |
|---|---|---|---|
| 5,452,416 A | 9/1995 | Hilton et al. | |
| 6,674,879 B1 | 1/2004 | Weisman et al. | |
| 7,120,276 B1 * | 10/2006 | Brady et al. | 382/107 |
| 7,146,372 B2 | 12/2006 | Bacus et al. | |
| 7,174,515 B1 | 2/2007 | Marshall et al. | |
| 7,577,282 B2 | 8/2009 | Gkanatsios et al. | |
| 7,611,452 B2 * | 11/2009 | Allison et al. | 600/1 |
| 7,616,801 B2 * | 11/2009 | Gkanatsios et al. | 382/132 |
| 7,672,495 B2 | 3/2010 | Evertsz et al. | |
| 7,760,924 B2 | 7/2010 | Ruth et al. | |
| 7,792,338 B2 | 9/2010 | Bacus et al. | |
| 7,796,793 B2 | 9/2010 | Luo | |

(Continued)

FOREIGN PATENT DOCUMENTS

JP    2006101975    4/2006

OTHER PUBLICATIONS

Kopanos, Daniel B., Chapter 28 Digital Breast Tomosynthesis, Breast Imaging 3rd edition, 2006 pp. 1065-1081, © 2007.

*Primary Examiner* — Xiomar Bautista
(74) *Attorney, Agent, or Firm* — Myers Bigel Sibley & Sajovec, P.A.

(57) ABSTRACT

Systems and methods for generating images of respective patients from multi-dimensional medical image data sets include a processor circuit in communication with a display having a graphic user interface (GUI), the processor circuit configured to define at least one grouping of a subset of slices selected from slices in a medical data stack, then generate and display at least one slabbed view based on the at least one grouping of slices.

20 Claims, 7 Drawing Sheets

U.S. PATENT DOCUMENTS

| | | |
|---|---|---|
| 7,809,175 B2 | 10/2010 | Roehrig et al. |
| 2003/0026470 A1* | 2/2003 | Kasai ............................ 382/132 |
| 2004/0015080 A1 | 1/2004 | Kelly et al. |
| 2004/0100476 A1 | 5/2004 | Morita et al. |
| 2004/0171924 A1 | 9/2004 | Mire et al. |
| 2005/0018891 A1 | 1/2005 | Barfuss et al. |
| 2005/0065424 A1 | 3/2005 | Shah et al. |
| 2005/0089205 A1 | 4/2005 | Kapur et al. |
| 2005/0107695 A1 | 5/2005 | Kiraly et al. |
| 2005/0197568 A1 | 9/2005 | Vass et al. |
| 2005/0215854 A1 | 9/2005 | Ozaki et al. |
| 2006/0058647 A1 | 3/2006 | Strommer et al. |
| 2006/0098855 A1 | 5/2006 | Gkanatsios et al. |
| 2006/0122467 A1 | 6/2006 | Harrington et al. |
| 2006/0171573 A1 | 8/2006 | Rogers |
| 2006/0210131 A1 | 9/2006 | Wheeler et al. |
| 2006/0215894 A1 | 9/2006 | Lakare |
| 2006/0228036 A1* | 10/2006 | Avinash ........................ 382/254 |
| 2006/0257009 A1* | 11/2006 | Wang et al. .................... 382/128 |
| 2007/0036402 A1* | 2/2007 | Cahill et al. ................... 382/128 |
| 2007/0038085 A1* | 2/2007 | Zhang et al. ................... 600/437 |
| 2007/0197909 A1 | 8/2007 | Kariathungal et al. |
| 2007/0237372 A1 | 10/2007 | Chen et al. |
| 2007/0274585 A1 | 11/2007 | Zhang et al. |
| 2008/0019581 A1 | 1/2008 | Gkanatsios et al. |
| 2008/0152086 A1 | 6/2008 | Hall et al. |
| 2008/0155468 A1 | 6/2008 | Rosander et al. |
| 2008/0246768 A1* | 10/2008 | Murray et al. ................. 345/427 |
| 2009/0029966 A1* | 1/2009 | Donawho et al. ......... 514/210.21 |

* cited by examiner

US 7,992,100 B2

DYNAMIC SLABBING TO RENDER VIEWS OF MEDICAL IMAGE DATA

RELATED APPLICATIONS

This application claims priority to U.S. Provisional Application Ser. No. 60/871,247, filed Dec. 21, 2006, the contents of which are hereby incorporated by reference as if recited in full herein.

FIELD OF THE INVENTION

The present invention relates to renderings of medical imaging data.

BACKGROUND OF THE INVENTION

Mammography is a medical imaging technique used to screen for breast cancer and other abnormalities in breast tissue. Traditionally, mammography images, referred to as mammograms, have been 2D images. Unlike the conventional mammogram, X-ray tomosynthesis is a mammography technique that creates a 3D representation of the breast. See, e.g., US2006/0098855. A typical mode for viewing such a 3D model is by browsing a series of (parallel) 2D images, referred to as "a stack." A 2D image in a stack is also referred to as a slice.

The diagnostic viewing of digital mammography images is typically performed in a Picture Archiving and Communication System (PACS). A main task of the PACS is to provide a highly efficient workflow for the health professional to review the images. The desire for high diagnostic throughput is particularly pertinent in the case of mammography screening, where an entire population of women can undergo mammography imaging. Within a few seconds, the reading physician should be able to come to the conclusion whether the breast is healthy or contains suspicious findings that should be further analyzed. When tomosynthesis images are used, a whole stack of 2D images must be reviewed for each breast instead, in contrast to conventional review of just a single 2D image. The tomosynthesis technique may potentially multiply the required review time by the number of images in the stack. Therefore, it is of great interest to create navigation tools for tomosynthesis images that can increase the speed of the review process.

One conventionally important part of the diagnostic assessment of the mammography images is to compare two breast images. To do so, the right and left breast are typically displayed simultaneously in a mirrored setup to allow a relatively simple visual comparison. Typically, the radiologist looks for symmetry between the right and left breast. Asymmetry could suggest that the images should be reviewed closer. A comparison of the new image(s) with older images is also highly useful and is common practice if older images exist.

The ability to have automatic geometric position synchronization between different stacks is a known PACS function, in a Sectra® PACS product/system it is known as the "Localizer". It is believed that this feature is limited to stacks that have a known geometric relation, typically several scans in between which the patient did not move, which in the DICOM standard is denoted by the "Frame of reference" attribute. Geometric position synchronization of stacks without limitations is also a conventional Sectra® PACS function, but the user manually defines a common reference point for the two data sets.

Computer Aided Detection (CAD) refers to computer-based image analysis methods that automatically identify suspected abnormalities, their location and other characteristics. CAD has proven to be useful for mammography screening, primarily as a complement to manual review. A typical work flow is that the mammograms undergo CAD analysis before manual review, where the CAD algorithm creates marks that are accessible by the physician during the manual review.

Despite the above, there is a need to provide systems and methods that can generate views that improve the accuracy, speed and/or quality of the diagnostic assessment.

SUMMARY OF EMBODIMENTS OF THE INVENTION

Embodiments of the present invention are directed to methods, systems and computer program products that can facilitate diagnostic reviews of medical images. Embodiments of the present invention may be particularly suitable for analysis of tomosynthesis mammograms.

Embodiments of the invention are particularly suitable for PACS, the invention is, however, more generally applicable, and should not be interpreted to be limited to PACS.

Some embodiments are directed to interactive visualization systems for rendering images of respective patients from a multi-dimensional medical image data set.

Embodiments of the invention are directed to interactive visualization systems for generating images of respective patients from multi-dimensional medical image data sets. The systems include a signal processor circuit in communication with a display having a graphic user interface (GUI), the processor circuit configured to define at least one grouping of a subset of slices selected from slices in a medical data stack, then generate and display at least one view of a part of the data set within a volumetric region defined by the at least one grouping of slices.

The generated and displayed view can be a slabbed view based on the at least one grouping of slices.

The medical image data set can include a tomosynthesis mammography data set.

In some embodiments, the processor circuit is configured to employ Computer Aided Detection (CAD) to electronically analyze and identify suspected abnormalities in slices of the medical image data stack, and wherein the circuit is configured to define a plurality of initial groupings of different stack slices based on data from the CAD identification.

The system can be configured so that the number of slices in a respective initial grouping of slices is less where there is at least one CAD identified suspected abnormality relative to the number of slices in initial slice groupings that do have not have at least one CAD identified suspected abnormality.

The system can be configured so that the GUI allows a user to refine a slabbed view whereby the current group of slices associated with that slabbed view is split into a plurality of separate smaller groups of slices and/or iteratively into a single slice view.

In particular embodiments, the circuit can be configured to generate a grouping of slices using CAD to identify clusters of microcalcifications such that each cluster is substantially entirely within a single grouping.

In some embodiments, the circuit is configured to provide an electronic review wizard with an automated viewing protocol that allows a user to browse slabbed views.

Other embodiments are directed to methods of generating views of medical data. The methods include: (a) electronically generating groups of slices from a stack of slices; (b)

combining pixel values associated with a common position in each slice of a respective group; and (c) generating slabbed views, one for each of the respective grouped slices, based on the combined pixel values.

The methods can also include refining at least one of the slabbed views into different sub-groupings of the original group of slices for the refined slabbed view.

Still other embodiments are directed to signal processor circuits for generating medical diagnostic views of a tomosynthesis stack of mammography patient image data. The circuit is configured to: (a) communicate with a graphical user interface (GUI) associated with a client workstation to accept user input to interact with the image data to generate desired views of the image data, and (b) generate and allow a user to browse slabbed views of breast tissue.

Yet other embodiments are directed to computer program products for providing a physician interactive access to patient medical data for rendering diagnostic medical images. The computer program product includes a computer readable storage medium having computer readable program code embodied in the medium. The computer-readable program code includes computer readable program code configured to define groups of slices of a medical image data stack together; and computer readable program code configured to generate a respective slabbed view for each of the groups of slices.

It is noted that any of the features claimed with respect to one type of claim, such as a system, apparatus, or computer program, may be claimed or carried out as any of the other types of claimed operations or features.

Further features, advantages and details of the present invention will be appreciated by those of ordinary skill in the art from a reading of the figures and the detailed description of the preferred embodiments that follow, such description being merely illustrative of the present invention.

BRIEF DESCRIPTION OF THE DRAWINGS

FIG. 3A illustrates a geometric reference point identified in each of the stacks. FIG. 3B illustrates that the anatomical regions in the two data sets can be electronically connected, correlated or linked according to embodiments of the present invention.

DETAILED DESCRIPTION OF EMBODIMENTS OF THE INVENTION

Figure 1:
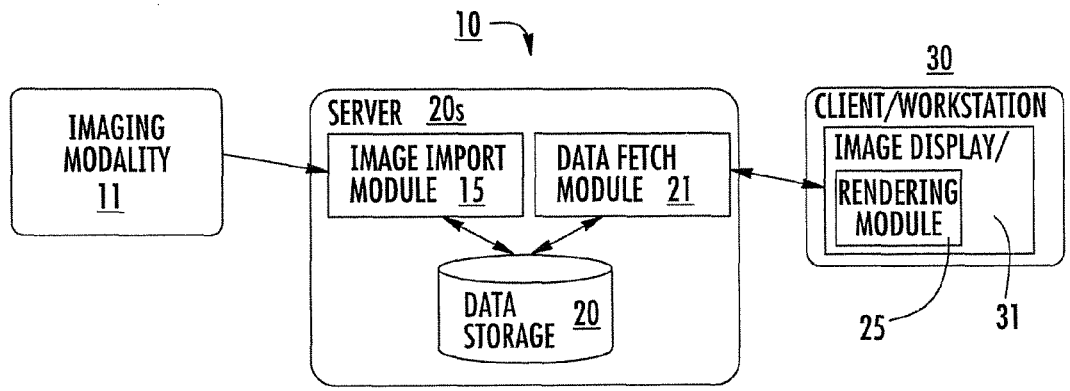
FIG. 1 is a schematic diagram of an electronic visualization system that can be used to render and display (medical) images

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise. In the claims, the claimed methods are not limited to the order of any steps recited unless so stated thereat.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

"Navigation" refers to electronically moving between different views of the data set. The most straight-forward navigation is to switch which slice is shown by the main display, but it may also mean reconstructing other representative images from the data set, such as slabbing a number of slices, constructing maximum-value slabs in arbitrary direction (known as Maximum Intensity Projection or "MIP"), constructing 2D slices in an arbitrary or direction different from the slices (known as Multiplanar Reconstruction, MPR), semi-transparent renderings of 3D regions using Direct Volume Rendering, and other methods. Below, X and Y dimensions refer to the plane of a 2D image, whereas the Z dimension refers to the direction perpendicular to X and Y.

The term "Direct Volume Rendering" or DVR is well known to those of skill in the art. DVR comprises electronically rendering a medical image directly from data sets to thereby display visualizations of target regions of the body, which can include color as well as internal structures, using multi-dimensional 3D or 4D or more dimensional data. In contrast to conventional iso-surface graphic constructs, DVR does not require the use of intermediate graphic constructs (such as polygons or triangles) to represent objects, surfaces and/or boundaries. However, DVR can use mathematical models to classify certain structures and can use graphic constructs.

Also, although embodiments of the present invention are directed to X-ray tomosynthesis, other 3-D image generation techniques and other image data may also be used.

The term "automatically" means that the operation can be substantially, and typically entirely, carried out without human or manual input, and is typically programmatically (via computer program control) directed or carried out. The term "electronically" includes both wireless and wired connections between components.

The term "synchronized" and derivatives thereof means that the same operation is applied to two or more views, generally, if not substantially or totally, concurrently. Synchronization is different from registration, where two volumes are merely aligned. The synchronization operation can be carried out between at least two different sets of image data, where an operation on a view rendered from a first data set is automatically synchronized (applied) to the same view as rendered from a different second image data set. It is noted that there can be any number of views in a synch group. Further, the synchronization does not require a static "master-slave" relationship between the images. For example, particularly, where two tomosynthesis data sets are synched, if an operation on image 1 is synched to image 2, then an operation on image 2 can also be synched to image 1 as well. In addition, in some embodiments, there can be several synch groups defined, and the synch operation can be applied across all groups, between defined groups, or within a single group, at the same time.

The term "slabbing" and derivatives thereof refer to a merging of two or more image slices in a stack and may, for example, use the maximum, minimum, median or average slice pixel value or other valuation of a combination or accumulation of the individual pixel values in the synch slices included in a respective slab.

The term "Computer Aided Detection (CAD)" refers to computer-based image analysis methods that automatically identify suspected abnormalities, their location and possibly other visual or anatomical characteristics.

The term "clinician" means physician, radiologist, physicist, or other medical personnel desiring to review medical data of a patient. The term "tissue" means anatomical entities such as organs, blood vessels, bone and the like.

Visualization means to present medical images to a user/clinician for viewing. The visualization can be in a flat 2-D and/or in 2-D what appears to be 3-D images on a display, data representing features with different visual characteristics such as with differing intensity, opacity, color, texture and the like. The images as presented by the visualization do not have to be the same as the original construct (i.e., they do not have to be the same 2-D slices from the imaging modality). Two common visualization techniques (apart from viewing original slices) are Multiplanar Reconstruction (MPR), which shows an arbitrary oblique slice through the anatomy and Maximum Intensity Projection (MIP) where a slab is visualized by displaying the maximum value "seen" from each image pixel. For MPR, there are a number of variants, the slice can be thin or constructed by averaging a thicker slab, etc . . . .

A data set can be defined as a number of grid points in G dimensions, where there is V number of values in each grid point. The term "multi-dimensional" refers to both components, grid G and variates V, of the data sets. For data sets having a V≧1, the data set is referred to as multi-variate. For example, normal medical data sets have G=3 and V=1.

The term "primary" refers to a data set or images or views generated based thereon, that is different from the reference data set, and is typically the more recent (or current) data set or the data set with a potential tissue irregularity.

The term "vicinity mark(s)" refers to an electronically generated mark that represents a feature, abnormality or irregularity associated with a different view or a different slice from the current view, that would not normally be shown or appear in the current view. As such, the vicinity mark can represent a feature in close spatial proximity or relationship to visually alert the user/clinician that a relevant feature may be in a different view.

In the description that follows, a client-server setup is illustrated, but the data retrieval interfaces contemplated by the instant invention may be implemented within one computer as well. The term "client" will be used both to denote a computer and the software (application) running on the computer. Additional computers can be used including more than one server and/or more than one client for a workstation. For example, the server can be more than one server with different functions carried out by or between different servers, such as the patient data short or long-term storage can be on one or more separate servers. The terms "display circuit" and/or "processor circuit" refer to software and/or hardware components that generate a view of image data for display. The circuits may be implemented using a variety of hardware and software. For example, operations of the display and/or processor circuit may be implemented using special-purpose hardware, such as an Application Specific Integrated Circuit (ASIC) and programmable logic devices such as gate arrays, and/or software or firmware running on a computing device such as a microprocessor, microcontroller or digital signal processor (DSP). The display and/or processor circuit is not limited to a graphics card or similar hardware and portions of the circuit may reside on different components of the visualization system.

Turning now to FIG. 1, an exemplary visualization system 10 is illustrated. As known to those of skill in the art, the system 10 can include at least one server 20s with an image import module 15, patient data storage 20, a data fetch module 21, a client (and/or workstation) 30 and a rendering system 25. The visualization system 10 can be in communication with at least one imaging modality 11 that electronically obtains respective volume data sets of patients and can electronically transfer the data sets to the electronic storage 20. The imaging modality 11 can be any desirable modality such as, but not limited to, NMR, MRI, ultrasound, and X-ray of any type, including, for example, tomosynthesis. Computed Tomography (CT) and fluoroscopy. Typically, for mammograms, the modality is of X-ray type. The visualization system 10 may also operate to render images using data sets from more than one of these modalities. That is, the visualization system 10 may be configured to render images irrespective of the imaging modality data type (i.e., a common system may render images for both CT and MRI volume image data). In some embodiments, the system 10 may optionally combine image data sets generated from different imaging modalities 11 to generate a combination image for a patient.

The rendering system 25 can be in communication with a physician workstation 30 to allow user input (typically graphical user input ("GUI")) and interactive collaboration of image rendering to give the physician alternate image views of the desired features in generally, typically substantially, real time. The rendering system 25 can be configured to zoom, rotate, and otherwise translate to give the physician visualization of the patient data in one or more views, such as section, front, back, top, bottom, and perspective views. The rendering system 25 may be wholly or partially incorporated into the physician workstation 30, or can be a remote or local module (or a combination remote and local module) component or circuit that can communicate with a plurality of physician workstations (not shown). The visualization system can employ a computer network and may be particularly suitable for clinical data exchange/transmission over an intranet. A respective workstation 30 can include at least one display 31 (and may employ two or more adjacent displays). The workstation 30 and/or rendering system 25 form part of an image processor system that includes a digital signal processor and other circuit components that allow for collaborative interactive user input using the display at the workstation 30. Thus, in operation, the image processor system renders the visualization of the medical image using the medical image volume data, typically on at least one display at the physician workstation 30.

Figure 2:
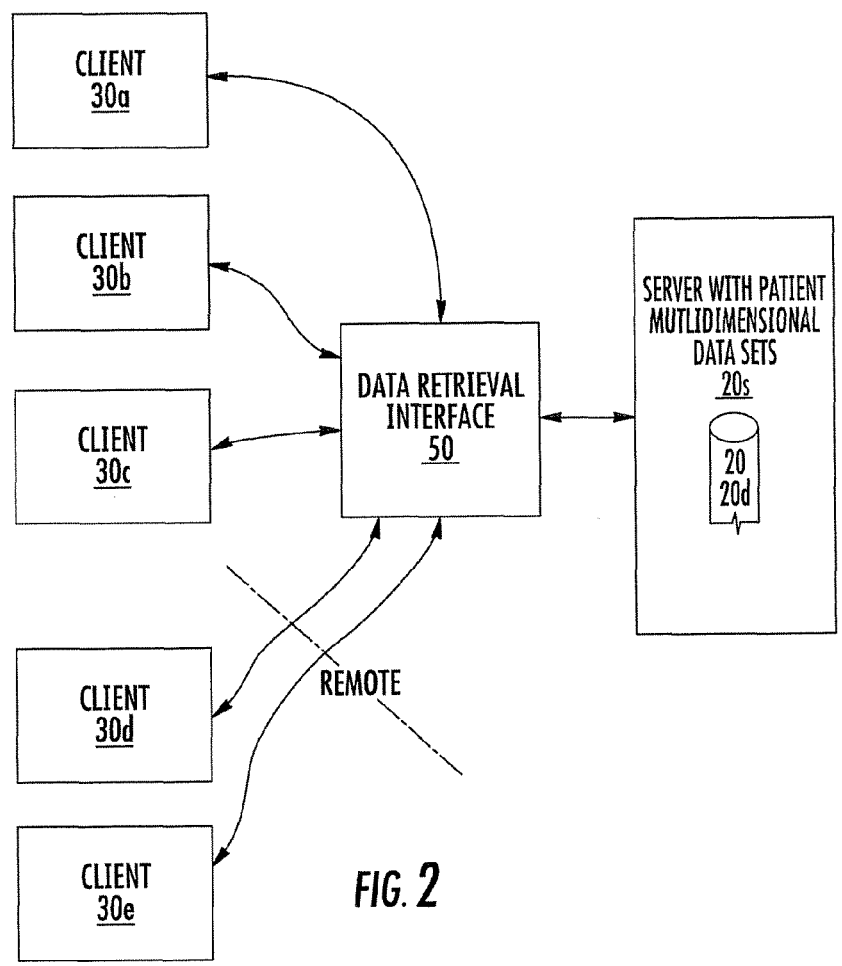
FIG. 2 is a schematic illustration of an imaging visualization system such as a PACS according to embodiments of the present invention.

As shown in FIG. 2, each respective workstation 30 can be described as a client 30 (shown as 30a, 30b, 30c, . . . 30e) that communicates with at least one (hub or remote) server 20s that stores the patient data sets or is in communication with the stored patient electronic data files 20. Additional numbers of clients 30 may be in communication with the server 20s and more than one server 20s may be used to store patient data. A data retrieval interface 50 can be used to communicate with the clients 30a-30e and the stored data sets on and/or accessible via server 20s. Some of the clients, shown as clients 30a, 30b, 30c can be local (within a common clinic or facility) and can access the data sets via a relatively broadband high speed connection using, for example, a LAN, while others, shown as clients 30d, 30e, designated by the broken line, may be remote and/or may have lesser bandwidth and/or speed, and for example, may access the data sets via a WAN and/or the Internet. Firewalls may be provided as appropriate for security.

For ease of discussion, the data retrieval interface 50 is shown as a stand-alone module or circuit. However, the interface 50 can be disposed partially on each client 30, partially or wholly on the server 20s, or may be configured as a discrete data retrieval interface server 50s (not shown). The clients 30, server 20s and/or interface 50 can each include a digital signal processor, circuit and/or module that can carry out aspects of the present invention. As shown in FIG. 2, all or selected ones of the clients 30a-30e can be online at the same time and may each repeatedly communicate with the data retrieval interface 50 to request volume image data, potentially resulting in a speed penalty and inhibiting fast system performance.

Figures 3A, 3B:
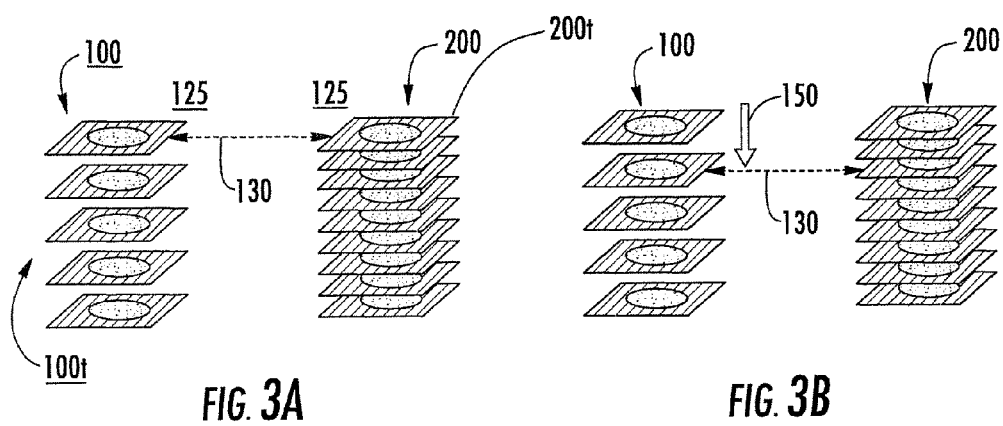
FIGS. 3A and 3B are schematic illustrations of two tomosynthesis stacks of patient image slices.

Embodiments of the invention are directed to visualization systems and methods that can define and display a view of the primary tomosynthesis stack, based on properties of the reference data set itself and/or properties of the current view of the reference data set. FIG. 3A illustrates a primary data set 200 that is a tomosynthesis stack and a reference data set 100 that is another image or stack of images for a breast. In the embodiment shown in FIGS. 3A and 3B, the reference data set 100 is also a tomosynthesis data set loot. In the embodiment shown in FIG. 4, the reference data set 100 can be a 2D reference image, such as a conventional mammogram. Views from both data sets can be shown in different parts of the same viewing application on a single display or on different displays. In some embodiments, the visualization system 10 can be configured to display a conventional reference mammogram, and corresponding views from a plurality of subsequent tomosynthesis stacks for comparing changes in density and symmetry, over time.

Embodiments of the invention can automatically define and display a view of the primary tomosynthesis stack, based on properties of the reference data set itself and/or properties of the current view of the reference data set. Such properties can be slice order number, known geometric/anatomic position, manually defined reference point corresponding to a point in the primary data set, but also results from an analysis of image content of the primary and reference data sets where comparable features can be identified in order to select the best view.

FIGS. 3A and 3B schematically illustrate a geometric/anatomic position in the case of two tomosynthesis stacks. FIG. 3A shows that a geometric (positional) reference point is identified (automatically or manually), connecting or linking 130 corresponding anatomical regions 125 in the two data sets 100, 200. FIG. 3B illustrates that navigation 150 in one stack 100t, 200t causes the corresponding navigation in the other stack. As shown in FIGS. 3A and 3B, the number of slices in each stack 100t, 200t does not need to be the same as the synchronization is connected to patient anatomy/data set geometry.

Figures 4A, 4B:
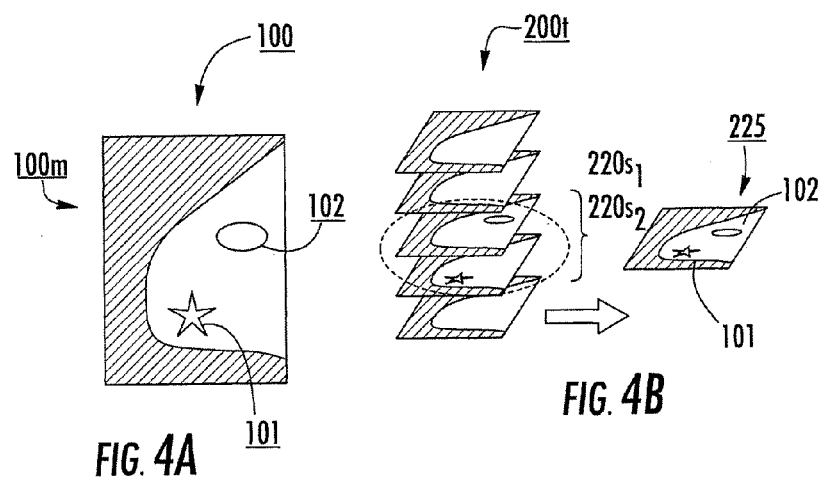
FIG. 4A illustrates a 2D reference image with salient image features.
FIG. 4B illustrates identification of features corresponding to those shown in FIG. 4A, in slices of a tomosynthesis stack, with the identified slices being electronically slabbed to generate a view according to embodiments of the present invention.

FIGS. 4A and 4B illustrate another embodiment, where the reference image data set 100 is a 2D mammogram image, a relatively common case when comparing a new tomosynthesis stack 200 with a conventional 2D mammogram (a prior). It is contemplated that a particularly useful application of some embodiments of the invention can be the ability to find a view of the primary tomosynthesis data set that well corresponds to the 2D mammogram, so as to present the corresponding anatomical region in a similar way. The view can be a certain slice selected from the stack, a plurality of discrete slices, a slabbed view of a set of slices or an MPR slice in another direction.

FIGS. 4A and 4B illustrate that embodiments of the invention can find a tomosynthesis view corresponding to the 2D reference image 100m. FIG. 4A shows a 2D reference image 100m with two salient image features 101, 102.

FIG. 4B illustrates the corresponding features are identified in two slices $220s_1$, $220s_2$ of the primary tomosynthesis stack 200. As shown, the best corresponding view is identified as a maximum value-slab 225 of the two slices $220s_1$, $220s_2$.

Figure 5:
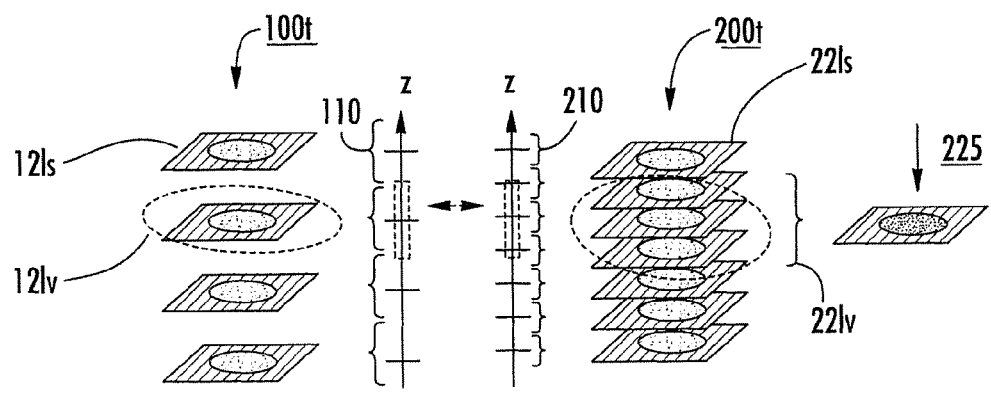
FIG. 5 is a schematic illustration of matching anatomical extent to a range in a Z dimension to slices in each tomosynthesis stack according to embodiments of the present invention.

As described above with respect to FIGS. 3A and 3B, in other embodiments, the reference data set 100 is also a tomosynthesis stack 100t. This can occur in a new image⇔prior image situation, or a left breast⇔right breast comparison within a new examination. The arrows represent work flow or navigation between views. In this case, the system can be configured to create a view of the primary data set 200 that substantially corresponds to the current view of the reference data set 100, for instance where the anatomical extent of the reference view is matched in the primary view. FIG. 5 illustrates that each stack 100t, 200t may include different numbers of slices. Each slice in the reference data set 121s covers a larger anatomical extent 110 in the Z direction relative to the slices 221s in the primary data stack 200t and their smaller anatomical extents 210.

FIG. 5 schematically illustrates an example of matching anatomical extent. One view 121v is selected from the reference stack 100t, corresponding to a range in the Z dimension. The synchronized primary view 221v to the right automatically finds the best match of the Z dimension extent, in this case a slab 225 of three slices 221s.

Figure 6:
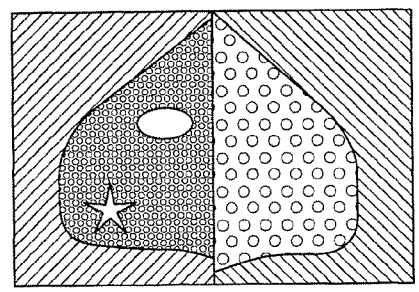
FIG. 6 illustrates mirroring two views about a vertical axis for visual comparison according to embodiments of the invention.

In some embodiments, the system 10 can be configured so that the primary data set 200 can be rotated and flipped according to the reference data set 100, for instance to create a mirror image setup for easy visual comparison. Mirroring can be applied both to new and old views of the same breast and to views of the left and right breast. FIG. 6 illustrates mirroring two views across a vertical axis for simple comparison.

In some embodiments, the system can be configured so that interaction with either of the data sets 100, 200 can be configured to create a corresponding change of the other data set automatically. For example, browsing to another slice in the primary data set 200 can cause a resynchronization of the reference data set 100 at the new slice's geometric position. In other words, the synchronization is not required to be a one-time occurrence but rather a mode of viewing that is active until explicitly interrupted. Other viewing settings can also be connected to synchronization, such as grayscale window/level setting, zoom, rotation, flip, panning, etc.

Figures 7A, 7B:
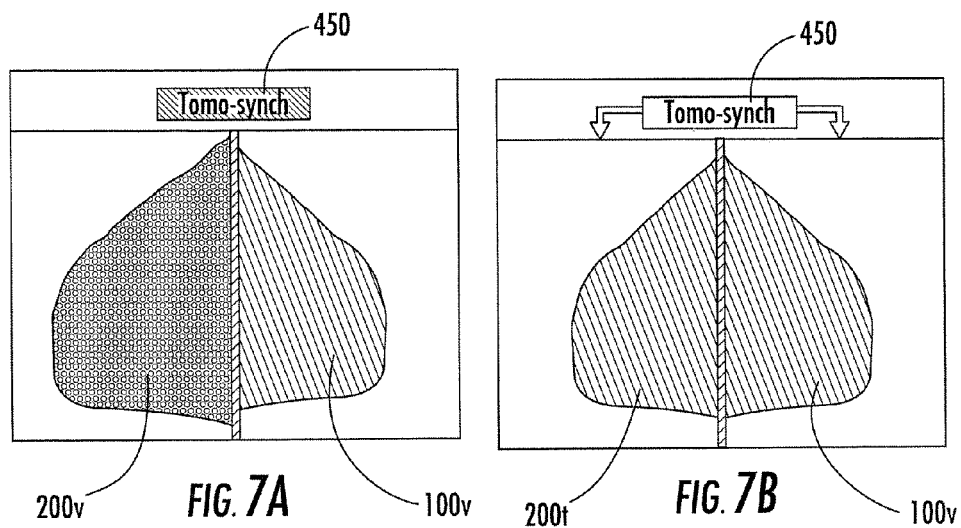
FIG. 7A illustrates a display with a visual tomo-synch mode alert according to embodiments of the invention.
FIG. 7B illustrates a display with a visual tomo-synch mode alert and a user interface (typically a GUI) to allow a user to activate or reapply a tomo-synch mode.

To alert a user as whether the tailored comparison view is active or not between the two data sets, an alert (audio and/or visual feedback) can be generated/displayed. For example, visual indicia viewable through a GUI, such as displaying an active icon or symbol in color, or displaying a header or footer with the active comparison mode visually indicated as "on" or "off". Audio output may also be used as appropriate (particularly after initial activation by a user, the mode is automatically disengaged because of the user's browsing of the primary tomosynthesis data set when the reference data set is a 2D image). FIG. 7A illustrates a display 30 showing a reference view 100v and a primary view 200v with the automated comparison viewing mode inactivated (Tomo Synch mode is off), while FIG. 7B illustrates the viewing mode activated as indicated by visual indicator 450 (shown as lit graphic "Tomo Synch" noting the active mode) in FIG. 7B.

One example is that a first comparable view of a tomosynthesis stack 200t and a 2D mammogram 100m is created, then the user browses the tomosynthesis stack 200t. This means that the electronic correlation or connection between the data sets may be broken, which can be indicated to the user. On the other hand, if the reference data set is another tomosynthesis stack 100t, then the corresponding browsing or view regeneration may be done there as well and the comparability can remain intact.

It is contemplated that a desired viewing format will be the traditional way of browsing through a stack of slices, but the efficiency may be increased by reducing the number of slices as much as practicable. Thus, slabbing or otherwise grouping slices (of oblique views or neighborhood based analysis) can be useful, if applied in a way to preserve diagnostically important features. A subset of slices from a data set can be selected and grouped, then a corresponding image can be generated and displayed of that part of the data set within a volumetric region defined by the at least one grouping of slices.

Slabbing can be defined mathematically as follows. A group of n 2D slice images defines a set, this set is denoted by I. For an arbitrary pixel position (x,y), mutual for all slices, the corresponding value of each slice is defined as $v_i$. Thus, for the entire group, an array can be defined as:

$$\bar{v} = (v_1, v_2, \ldots, v_n). \quad \text{Equation 1}$$

The pixel value for the joint view of the whole group is constructed by a function $f(v)$, applied individually to all pixel positions of the slices. Average value slabbing is achieved by:

$$f(\bar{v}) = \sum_{i=1}^{n} v_i / n. \quad \text{Equation 2}$$

Maximum value slabbing is achieved by:

$$f(\bar{v}) = \max_{i \in I}(v_i). \quad \text{Equation 3}$$

Figure 8:
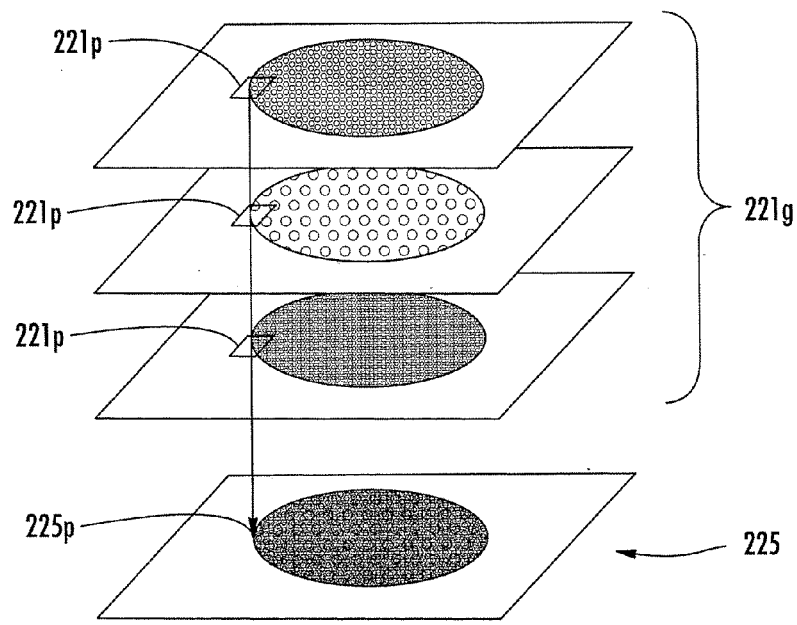
FIG. 8 is a schematic illustration of a slabbing technique according to embodiments of the present invention.

FIG. 8 illustrates a group of slices 221g having a pixel position 221p identified and/or marked and used to render a slabbed view 225. In the slabbed view 225, each pixel 225p is a combination of the pixel values at the corresponding pixel position of the slices in the group 221g. A common size of a 2D mammogram is in the range of millions of pixels, typically about 3328×2560 pixels (8.5 million pixels).

In some embodiments, data dependent slabbing can be used for efficient analysis, rendering and/or reading of medical image stacks. An exemplary workflow would be as shown schematically in FIGS. 9A-9D.

Figures 9A, 9B, 9C, 9D:
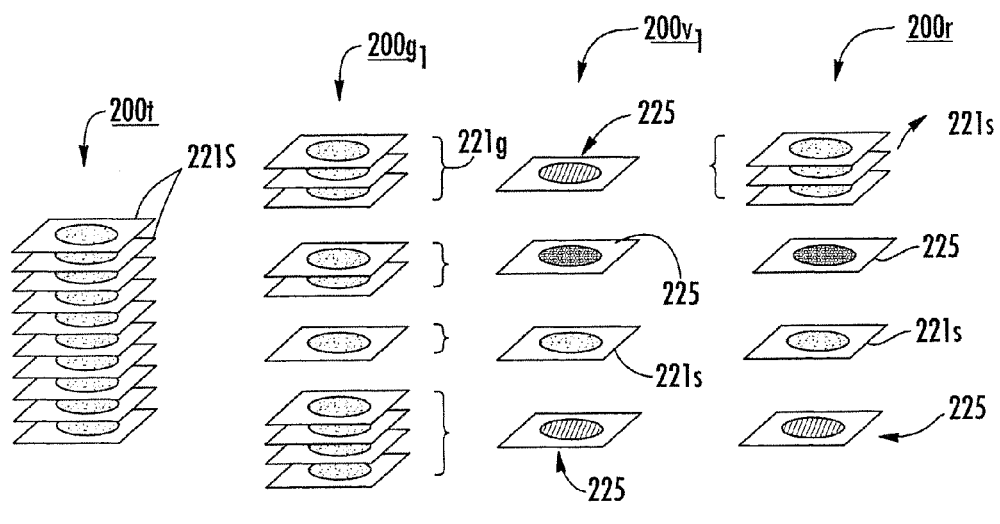
FIGS. 9A-9D illustrate a series of operations that can be used to group slices in tomosynthesis stacks, view slices and slabs, and refine views to different sub-groups and/or original slice views according to embodiments of the present invention.

1. As shown in FIG. 9A, an original medical image data set, the stack, is electronically automatically analyzed for relevant or visually dominant features. For example, tissue intensity variation, dimpling, density, calcifications (e.g., microcalcifications and/or clusters thereof), abrupt transitions from neighborhoods of pixels, shapes or other optically or electronically detectable visual irregularities, and the like.
2. As shown in FIG. 9B, an initial grouping $200g_1$ of stack slices 221 is selected based on the result of the analysis. A plurality of groups of slices 221g are created. The group size (number or slices per group and number of groups) can vary. Typically, relatively small groups 221g are created when there are important features in the slices, and larger groups (larger numbers of slices) for less important features.

3. FIG. 9C illustrates an initial set of views are generated $200v_1$, one for each slice group $221g$. The view $200v1$ can include slabbed versions 225 of the grouped slices in the group. The slabbing can be constructed by various compositing algorithms, such as averaging, maximum value, minimum value, or others.
4. The user can view the data set by browsing the initial view $200v1$ with slab views 225.
5. FIG. 9D illustrates that a user may find an interesting slabbed view and decide to analyze it in more detail. This can be done by activating a refine mechanism (typically by pressing a key or clicking a button in the GUI), which splits the current slabbed group 225 group into several groups and/or into the original slices. The refinement can repeated until the slab views are undone to reveal the original slices (see top slab 225 in FIG. 9D which is back to the original slices $221s$ from the grouping in FIG. 9B).

The refinement can be applied to a single group or the whole stack at once. The refinement can go directly to original slices, or have intermediate steps. The groups may be overlapping.

The slice groups can be determined based on the outcome of a CAD algorithm. One usage is to have a maximum size of a slice group containing CAD findings. Another possibility is to make sure that similar and nearby CAD findings end up in the same slice group, a situation that may apply for clusters of micro-calcifications.

The described work flow can also be implemented as an automatic viewing protocol, which can be referred to as a "review wizard" that has a series of logical rules that define a list of view combinations and their layout. This can be an extension of the regular "hanging" protocols for PACSs, known as Default Display Protocols (DDPs). To review the whole data set, the user simply needs to press a key or click a button for each step through the wizard. The wizard can be defined to show the initial slice groups. The wizard can be defined to automatically show certain refinements. Apart from controlled browsing of slabbed stacks, the wizard may define other view sequences for the data set, including zoomed and panned views, different grayscale windows, with and without image processing algorithms applied, etc.

In some embodiments, the systems can implement an efficient work flow for diagnostic review of medical image stacks or volumes using CAD marks, where CAD marks are available to let the user navigate between views of the data set by means of location information from CAD marks.

CAD marks can be used in a number of ways to achieve desired navigation. In some embodiments, a viewing mode can include a simple or summary list of the CAD marks can be displayed adjacent to the main image view, preferably sorted according to location. The list entry may contain some of the available information about the mark. When the user selects a list entry, typically by clicking it, a representative view corresponding to this mark is shown on the display, typically in the main view. A variant of this mode is to list or show small images, thumbnails, for each mark or mark cluster, where the thumbnail shows a miniature of what the main view will show when this thumbnail is selected. To navigate to this view, the user selects (clicks) the thumbnail. The currently selected thumbnail can be visually marked in the list.

Figure 10A:
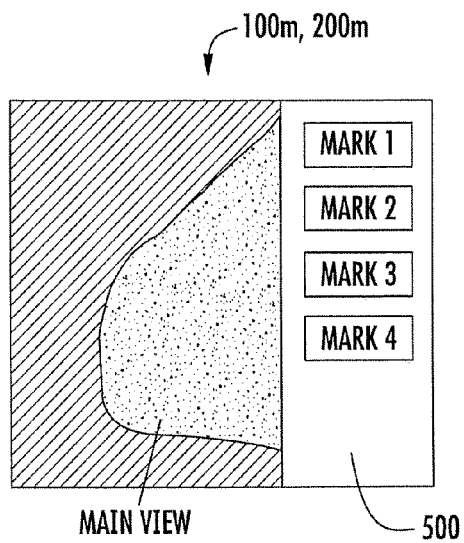
FIGS. 10A and 10B are schematic illustrations of a main view of a tomosynthesis data set with a list of identified CAD marks for ease of user review according to embodiments of the present invention.
Figure 10B:
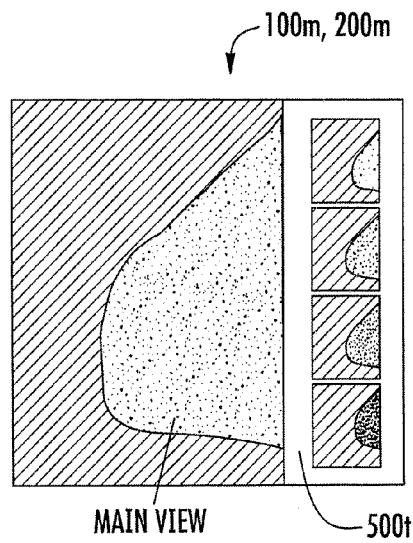

FIGS. 10A and 10B illustrate a main view $100m$, $200m$ of a reference or primary data set 100, 200. FIG. 10A also shows the use of a list of user-selectable marks that allow a user to generate the view(s) associated with the CAD mark selected. FIG. 10B illustrates a list of CAD mark thumbnails $500t$. Combinations of the visual thumbnails and list $500t$, 500 can also be used.

Figure 11A:
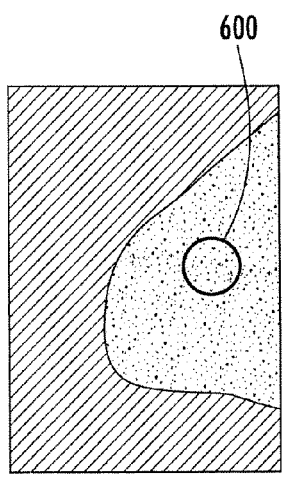
FIGS. 11A-11C illustrate rendered diagnostic views of patient image data using vicinity marks according to embodiments of the present invention.
Figure 11B:
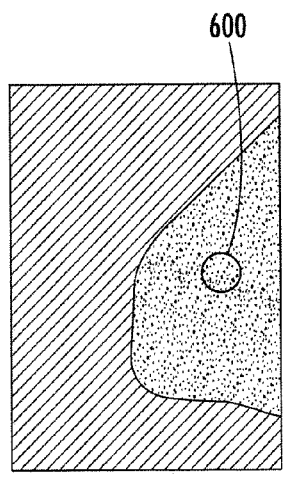
Figure 11C:
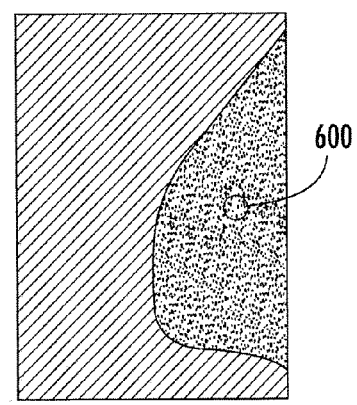

Other modes consist of (direct) interaction with the main view. To inform the user that there are CAD marks that do not belong in the currently shown view, but are located in the vicinity, such marks can be shown with a slightly different appearance relative to a mark "inside" the view. FIGS. 11A-11C, illustrate the use of vicinity marks 600. The vicinity marks 600 could, for instance, be shown in contrast, grayed out and/or have dashed or broken lines. The vicinity mark appearance could also depend on the distance from the current view, for increasing distance the marks could become fainter in color or smaller in size (as shown by the fainter color and smaller size from left to right in FIGS. 11A-11C). One example is a ring marker that could be modeled as sphere or ellipsoid, showing up as smaller circles in nearby views. The appearance can be made to differ if the exact position is "below or above" the current view (so that the user intuitively knows whether he/she should browse forward or backward to get to it). Regardless of the appearance, navigation can be achieved by the user selecting a vicinity mark, to advance toward, and typically directly switching to the view where the mark most properly belongs.

The CAD findings and/or marks can also be used as a base for an automatic viewing protocol, referred to as a review wizard that defines a list of view combinations and their layout. This can be seen as an extension of the regular "hanging" protocols for PACSs known as Default Display Protocols (DDPs). To review the whole data set, the user simply needs to press a key or click a button for each step through the wizard. The wizard can be defined to visit CAD marks in a certain order, for instance sorted by location or probability of abnormality. Apart from controlled browsing of CAD mark related views, the wizard may define other view sequences for the data set, including zoomed and panned views, different grayscale windows, with and without image processing algorithms applied, etc.

The CAD findings and/or marks used for navigation can be automatically clustered in relevant groups. For example, one clustering is to join all marks corresponding to the same slice in a group. There can also be separate marks that correspond to what a physician would refer to as a "single" feature, such as a cluster of microcalcifications. Joining marks from several slices into a group can be combined with the creation of a representative view to cover the entire region of interest defined by the marks from the several slices. Typical examples include slabbing (combining several slices into a single slice, typically by averaging) and 3D modeling such as DVR.

As will be appreciated by one of skill in the art, embodiments of the invention may be embodied as a method, system, data processing system, or computer program product. Accordingly, the present invention may take the form of an entirely software embodiment or an embodiment combining software and hardware aspects, all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic or other electronic storage devices.

Computer program code for carrying out operations of the present invention may be written in an object oriented programming language such as Java, Smalltalk or C++. However, the computer program code for carrying out operations of the present invention may also be written in conventional procedural programming languages, such as the "C" programming language or in a visually oriented programming environment, such as VisualBasic.

Certain of the program code may execute entirely on one or more of the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider). In some embodiments, some program code may execute on local computers and some program code may execute on one or more local and/or remote server. The communication can be done in real time or near real time or off-line using a volume data set provided from the imaging modality.

The invention is described in part below with reference to flowchart illustrations and/or block diagrams of methods, systems, computer program products and data and/or system architecture structures according to embodiments of the invention. It will be understood that each block of the illustrations, and/or combinations of blocks, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the block or blocks.

These computer program instructions may also be stored in a computer-readable memory or storage that can direct a computer or other programmable data processing apparatus to function in a particular manner, such that the instructions stored in the computer-readable memory or storage produce an article of manufacture including instruction means which implement the function/act specified in the block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the block or blocks.

Figure 12:
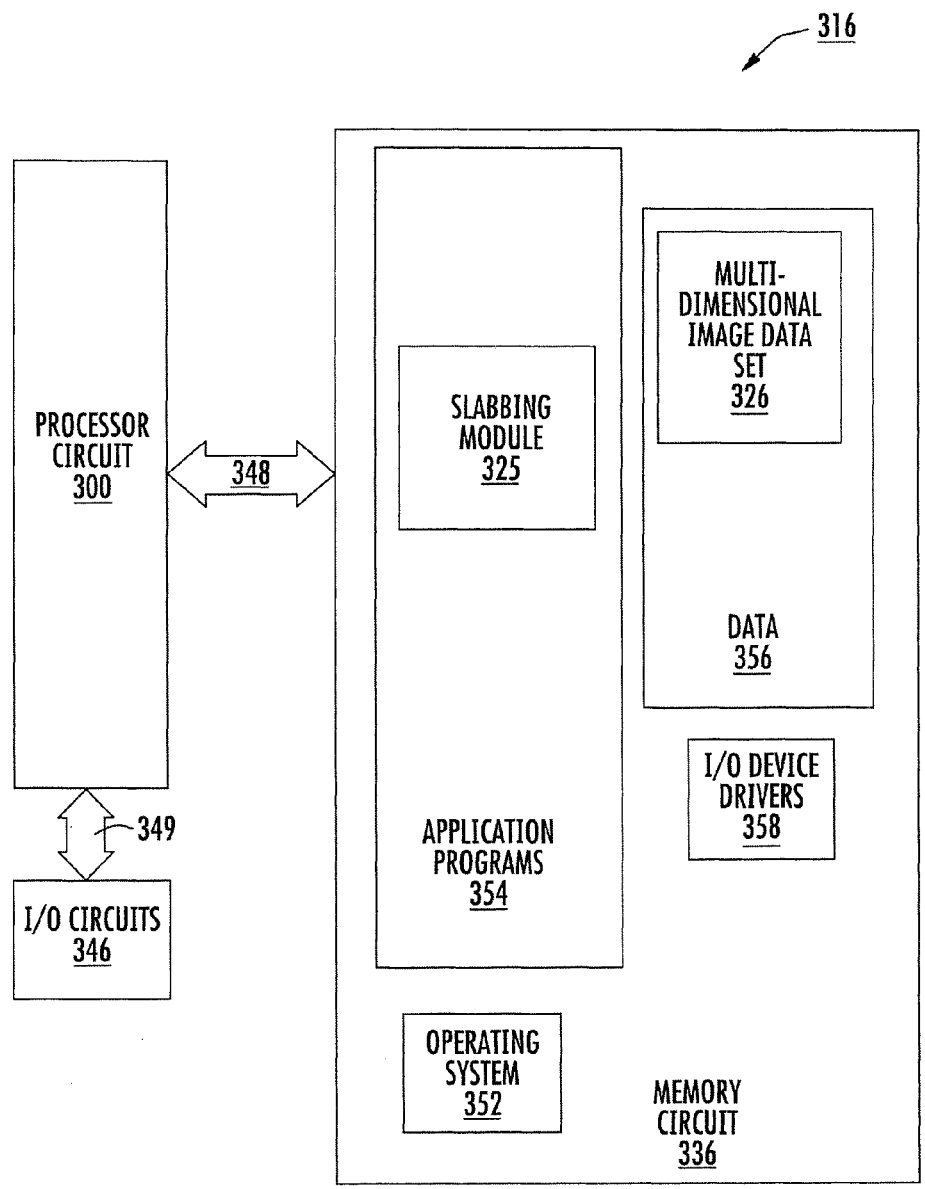
FIG. 12 is a block diagram of a data processing circuit or system according to embodiments of the present invention.

As illustrated in FIG. 12, embodiments of the invention may be configured as a data processing system 316, which can be used to carry out or direct operations of the rendering, and can include a processor circuit 300, a memory 336 and input/output circuits 346. The data processing system may be incorporated in, for example, one or more of a personal computer, workstation 316, server, router or the like. The system 316 can reside on one machine or between a plurality of machines. The processor 300 communicates with the memory 336 via an address/data bus 348 and communicates with the input/output circuits 346 via an address/data bus 349. The input/output circuits 346 can be used to transfer information between the memory (memory and/or storage media) 336 and another computer system or a network using, for example, an Internet protocol (IP) connection. These components may be conventional components such as those used in many conventional data processing systems, which may be configured to operate as described herein.

In particular, the processor 300 can be commercially available or custom microprocessor, microcontroller, digital signal processor or the like. The memory 336 may include any memory devices and/or storage media containing the software and data used to implement the functionality circuits or modules used in accordance with embodiments of the present invention. The memory 336 can include, but is not limited to, the following types of devices: ROM, PROM, EPROM, EEPROM, flash memory, SRAM, DRAM and magnetic disk. In some embodiments of the present invention, the memory 336 may be a content addressable memory (CAM).

As further illustrated in FIG. 12, the memory (and/or storage media) 336 may include several categories of software and data used in the data processing system: an operating system 352; application programs 354; input/output device drivers 358; and data 356. As will be appreciated by those of skill in the art, the operating system 352 may be any operating system suitable for use with a data processing system, such as IBM®, OS/2®, AIX® or zOS® operating systems or Microsoft® Windows®95, Windows98, Windows2000 or WindowsXP operating systems Unix or Linux™. IBM, OS/2, AIX and zOS are trademarks of International Business Machines Corporation in the United States, other countries, or both while Linux is a trademark of Linus Torvalds in the United States, other countries, or both. Microsoft and Windows are trademarks of Microsoft Corporation in the United States, other countries, or both. The input/output device drivers 358 typically include software routines accessed through the operating system 352 by the application programs 354 to communicate with devices such as the input/output circuits 346 and certain memory 336 components. The application programs 354 are illustrative of the programs that implement the various features of the circuits and modules according to some embodiments of the present invention. Finally, the data 356 represents the static and dynamic data used by the application programs 354 the operating system 352 the input/output device drivers 358 and other software programs that may reside in the memory 336.

The data 356 may include (archived or stored) multi-dimensional patient digital image data sets 326 that provides at least one stack of tomosynthesis image data correlated to respective patients. As further illustrated in FIG. 12, according to some embodiments of the present invention application programs 354 include a Slabbing Module 325. The application program 354 may be located in a local server (or processor) and/or database or a remote server (or processor) and/or database, or combinations of local and remote databases and/or servers.

While the present invention is illustrated with reference to the application programs 354 in FIG. 12, as will be appreciated by those of skill in the art, other configurations fall within the scope of the present invention. For example, rather than being application programs 354 these circuits and modules may also be incorporated into the operating system 352 or other such logical division of the data processing system. Furthermore, while the application program 354 is illustrated in a single data processing system, as will be appreciated by those of skill in the art, such functionality may be distributed across one or more data processing systems in, for example, the type of client/server arrangement described above. Thus, the present invention should not be construed as limited to the configurations illustrated in FIG. 12 but may be provided by other arrangements and/or divisions of functions between data processing systems. For example, although FIG. 12 is illustrated as having various circuits and modules, one or more of these circuits or modules may be combined or separated without departing from the scope of the present invention.

The circuit can be configured so that when displaying a tomosynthesis stack and a reference data set, to automatically generate a view of the tomosynthesis stack tailored for comparison with the current view of the reference data set. The automated analysis can use data set features and, if a geometric relation between the data sets is known, position landmarks, displayed in different parts of the same viewing application. The circuit can be configured, at user interaction with the primary tomosynthesis stack, to automatically update the view of the reference stack (the synchronization can be in the other direction as well). The circuit can be configured to generate a view of a slabbing of several slices, for instance a maximum or average slab. The view generated may include image manipulations such as rotating, flipping, panning, zooming, grayscale window/level setting. The automatic view generation can be a synchronization mode that is reapplied as the user interacts with the data sets. The circuit can be configured to display a visual mark to the user that states whether the tailored comparison view synch is active.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. An interactive visualization system for generating images of respective patients from multi-dimensional medical image data sets, comprising:
   a processor circuit in communication with a display having a graphic user interface (GUI), the processor circuit configured to employ Computer Aided Detection (CAD) to electronically analyze and identify suspected abnormalities in slices of the medical image data stack to automatically define at least one grouping of a subset of slices selected from slices in a medical data stack based on data from the CAD identification, then generate and display at least one slabbed view of a part of the data set within a volumetric region defined by the at least one grouping of slices with suspected abnormalities.

2. A system according to claim 1, wherein the medical image data set comprises a tomosynthesis mammography data set.

3. A system according to claim 2, wherein the circuit is configured to generate a grouping of slices using CAD to identify clusters of microcalcifications such that each cluster is substantially entirely within a single grouping.

4. A system according to claim 1, wherein the circuit is configured to generate a plurality of different initial groupings of the image slices and display a plurality of slabbed views of the initial groupings.

5. A system according to claim 4, wherein the number of slices in a respective initial grouping of slices is less where there is at least one CAD identified suspected abnormality relative to the number of slices in initial slice groupings that do have not have at least one CAD identified suspected abnormality.

6. A system according to claim 1, wherein the at least one grouping is a plurality of groupings of slices, wherein the processor circuit is configured to generate a plurality of slabbed views using different groupings of slices, and wherein the GUI is configured to allow a user to browse the different slabbed views.

7. A system according to claim 6, wherein the GUI is configured to allow a user to refine a slabbed view whereby the current group of slices associated with that slabbed view is split into a plurality of separate smaller groups of slices and/or iteratively into a single slice view.

8. A system according to claim 1, wherein the circuit is configured to provide an electronic review wizard with an automated viewing protocol that allows a user to browse the slabbed views.

9. A system according to claim 8, wherein the wizard is configured to display slabbed views of initial groupings and allow a user to select refinements of one or more of the initial groupings whereby a selected slabbed view is split into a plurality of separate smaller groups of slices and/or into a single slice view.

10. A system according to claim 8, wherein the wizard is configured to display the slabbed views of the initial groupings and automatically show refinements of the initial groupings whereby the current slabbed view being refined is split into a plurality of separate groups of slices and/or into a single slice view.

11. A system according to claim 1, wherein the at least one slabbed view is generated by taking the average of the pixel values at a corresponding position in different slices of a respective grouping.

12. A system according to claim 1, wherein the at least one slabbed view is generated by taking the maximum of the pixel values at a corresponding position in different slices of a respective grouping.

13. A system according to claim 1, wherein the at least one slabbed view is generated by taking the minimum of the pixel values at a corresponding position in different slices of a respective grouping.

14. A system according to claim 1, wherein the at least one slabbed view is generated by taking the median of the pixel values at a corresponding position in different slices of a respective grouping.

15. A method of generating views of medical data, comprising:
   electronically generating groups of slices from a stack of slices using Computer Aided Detection (CAD) to electronically analyze and identify suspected abnormalities in slices of the medical image data stack and automatically generate the groups of slices based on the CAD identification of abnormalities;
   combining pixel values associated with a common position in each slice of a respective group; and
   generating slabbed views, one for each of the respective grouped slices, based on the combined pixel values.

16. A method according to claim 15, further comprising refining at least one of the slabbed views into different sub-groupings of the original group of slices for the refined slabbed view.

17. A method according to claim 15, further comprising iteratively refining at least one of the slabbed views into smaller sub-groupings of slices and/or into single slices; then generating associated refined slabbed views.

18. A method according to claim 15, further comprising accepting user input to select to browse the slabbed views and to refine the slabbed views.

19. A processor circuit for generating medical diagnostic views of a tomosynthesis stack of mammography patient image data, wherein the circuit is configured to communicate with a graphical user interface (GUI) associated with a client workstation to accept user input to interact with the image data to generate desired views of the image data, and wherein the circuit is configured to employ Computer Aided Detection (CAD) to electronically analyze and identify suspected abnormalities in slices of the tomosynthesis image data stack to define groups of slices and to generate slabbed views of breast tissue with suspected abnormalities and allow a user to browse the slabbed views.

20. A computer program product for providing physician interactive access to patient medical data for rendering diagnostic medical images, the computer program product comprising:

a non-transitory computer readable storage medium having computer readable program code embodied in the medium, the computer-readable program code comprising:

computer readable program code configured to employ Computer Aided Detection (CAD) to electronically analyze and identify suspected abnormalities in slices of a stack of patient medical image data to define groups of slices of a medical image data stack; and computer readable program code configured to generate a respective slabbed view for each of the groups of slices with suspected abnormalities.

\* \* \* \* \*

UNITED STATES PATENT AND TRADEMARK OFFICE
CERTIFICATE OF CORRECTION

| | | |
|---|---|---|
| PATENT NO. | : 7,992,100 B2 | Page 1 of 1 |
| APPLICATION NO. | : 11/956422 | |
| DATED | : August 2, 2011 | |
| INVENTOR(S) | : Lundström et al. | |

It is certified that error appears in the above-identified patent and that said Letters Patent is hereby corrected as shown below:

On the Title Page:

Primary Examiner: Please correct "Xiomar Bautista"
       to read -- Xiomara Bautista --

In the Claims:
Column 15, Claim 5, Line 58:   Please correct "do have not have"
                                  to read -- do not have --

Signed and Sealed this

Thirteenth Day of December, 2011

David J. Kappos
*Director of the United States Patent and Trademark Office*